United States Patent [19]

Brazdil et al.

[11] Patent Number: 4,665,259
[45] Date of Patent: May 12, 1987

[54] METHANE CONVERSION PROCESS USING PHOSPHATE-CONTAINING CATALYSTS

[75] Inventors: James F. Brazdil, Mayfield Village; Raymond G. Teller, Aurora; Joseph P. Bartek, Highland Heights; Robert K. Grasselli, Aurora, all of Ohio

[73] Assignee: The Standard Oil Company, Cleveland, Ohio

[21] Appl. No.: 770,666

[22] Filed: Aug. 28, 1985

[51] Int. Cl.$^4$ .................................. C07C 2/00
[52] U.S. Cl. .................... 585/500; 585/415; 585/417; 585/541; 585/654; 585/656; 585/658; 585/661; 585/700; 585/943; 585/418
[58] Field of Search ............... 585/415, 417, 418, 500, 585/541, 654, 656, 658, 661, 700, 943

[56] References Cited

U.S. PATENT DOCUMENTS

| | | | |
|---|---|---|---|
| 3,324,195 | 5/1964 | Hwa et al. | 260/680 |
| 3,845,156 | 4/1972 | Farha, Jr. | 260/680 E |
| 3,980,580 | 1/1974 | Fox et al. | 252/186 |
| 4,067,921 | 12/1976 | Helberg | 260/680 R |
| 4,100,218 | 5/1977 | Chim | 260/673 |
| 4,120,910 | 12/1978 | Chu . | |
| 4,172,810 | 10/1980 | Mitchell, III et al. | 585/943 |
| 4,239,658 | 12/1980 | Mitchell, III et al. | 585/656 |
| 4,255,283 | 3/1981 | Bartek et al. | 252/437 |
| 4,310,717 | 5/1981 | Eastman et al. | 585/661 |
| 4,368,346 | 5/1983 | Eastman | 585/658 |
| 4,443,644 | 8/1983 | Jones et al. | 585/500 |
| 4,443,645 | 8/1983 | Jones et al. | 585/500 |
| 4,443,646 | 8/1983 | Jones et al. | 585/500 |
| 4,443,647 | 8/1983 | Jones et al. | 585/500 |
| 4,443,648 | 8/1983 | Jones et al. | 585/500 |
| 4,443,649 | 8/1983 | Jones et al. | 585/500 |
| 4,450,310 | 3/1983 | Fox et al. | 585/400 |
| 4,467,130 | 8/1984 | Olah | 585/500 |
| 4,489,215 | 4/1984 | Withers | 585/500 |
| 4,495,374 | 1/1983 | Jones et al. | 585/943 |
| 4,499,322 | 8/1985 | Jones et al. | 585/500 |
| 4,523,049 | 6/1985 | Jones et al. | 585/943 |
| 4,523,050 | 4/1985 | Jones et al. | 585/500 |
| 4,544,784 | 10/1985 | Sofranko et al. | 585/500 |

OTHER PUBLICATIONS

Fang, T. et al, Catalytic Pyrolysis of Methane, 265–273 (1981), Synthesis of Ethylene via Oxidative Coupling of Methane, Keller et al, pp. 9–19, 1982.
Hinsen et al., Oxidative Dehydrogenation and Coupling of Methane, 8th International Congress on Catalysis, vol. III, pp. 581–592, 1984.

Primary Examiner—William R. Dixon, Jr.
Assistant Examiner—Cynthia A. Prezlock
Attorney, Agent, or Firm—Larry W. Evans; David J. Untener; Raymond F. Keller

[57] ABSTRACT

A process is disclosed for converting methane to a higher order hydrocarbon comprising contacting a gaseous reactant comprising methane with a phosphate-containing catalyst for a sufficient period of time and at an effective temperature to provide said higher order hydrocarbon, said catalyst being represented by the formula $$M_xPO_y$$

wherein
M is selected from the group consisting of Pb, Bi, Sb, Sn, Tl, In, Mn, Cd, Ge or a mixture of two or more thereof,
x is from about 0.1 to about 10, and
y is the number of oxygens needed to fulfill the valence requirements of the other elements.

27 Claims, No Drawings

METHANE CONVERSION PROCESS USING PHOSPHATE-CONTAINING CATALYSTS

TECHNICAL FIELD

This invention relates to processes for converting methane to a higher order hydrocarbon. More particularly, this invention relates to a process for converting methane to a higher order hydrocarbon using a phosphate-containing catalyst. This process is particularly suitable for converting methane to ethane and/or ethylene.

BACKGROUND OF THE INVENTION

A major source of methane is natural gas which typically contains about 85% methane and about 10% ethane with the balance being made up of propane, the butanes, the pentanes and nitrogen. The term "higher order hydrocarbon" refers to a hydrocarbon having at least two carbon atoms.

Primary sources for natural gas are the porous reservoirs generally associated with crude oil reserves. From these sources come most of the natural gas used for heating purposes. Quantities of natural gas are also known to be present in coal deposits and are byproducts of crude oil refinery processes and bacterial decomposition of organic matter. Natural gas obtained from these sources is generally utilized as a fuel at the site.

Prior to commercial use, natural gas must be processed to remove water vapor, condensible hydrocarbons and inert or poisonous constituents. Condensible hydrocarbons are generally removed by cooling natural gas to a low temperature and then washing the natural gas with a cold hydrocarbon liquid to absorb the condensible hydrocarbons. The condensible hydrocarbons are typically ethane and heavier hydrocarbons. This gas processing can occur at the wellhead or at a central processing station. Processed natural gas typically comprises a major amount of methane, and minor amounts of ethane, propane, the butanes, the pentanes carbon dioxide and nitrogen. Generally, processed natural gas comprises from about 50% to more than about 95% by volume of methane. Natural gas is used principally as a source of heat in residential, commercial and industrial service.

Methane has a number of commercial uses in the chemical processing industry. The largest use of methane, other than as a primary fuel, is in the production of ammonia and methanol. Ammonia is a basic ingredient of fertilizers and is also a common feedstock in the production of petrochemicals such as acrylonitrile and nylon-6. Methanol is a precursor material for products such as formaldehyde, acetic acid and polyesters. Methane has also been used as a feedstock for the production of acetylene by electric-arc or partial-oxidation processes. Another commercial use for methane is in the production of halogenated products such as methyl chloride, methylene chloride, chloroform and carbon tetrachloride. Methane also reacts with ammonia to produce hydrogen cyanide.

Most processed natural gas is distributed through extensive pipeline distribution networks. As natural gas reserves in close proximity to gas usage decrease, new sources that are more distant require additional transportation. Many of these distant sources are not, however, amendable to transport by pipeline. For example, sources that are located in areas requiring economically unfeasible pipeline networks or in areas requiring transport across large bodies of water are not amendable to transport by pipeline. This problem has been addressed in several ways. One such solution has been to build a production facility at the site of the natural gas deposit to manufacture one specific product. This approach is limited as the natural gas can be used only for one product, preempting other feasible uses. Another approach has been to liquefy the natural gas and transport the liquid natural gas in specially designed tanker ships. Natural gas can be reduced to 1/600th of the volume occupied in the gaseous state by such cryogenic processing, and with proper procedures, safely stored or transported. These processes, which involve liquefying natural gas to a temperature of about −162° C., transporting the gas, and revaporizing it are complex and energy intensive.

Still another approach has been the conversion of natural gas to higher order hydrocarbons that can be easily handled and transported, preferably substantially liquid hydrocarbons. The conversion of natural gas to higher order hydrocarbons, especially ethane and ethylene, would retain the material's versatility for use as precursor materials in chemical processing. Known dehydrogenation and polymerization processes are available for the further conversion of ethane and ethylene to liquid hydrocarbons. In these ways, easily transportable commodities may be derived directly from natural gas at the wellhead. A drawback in implementing such processes has been in obtaining a sufficient conversion rate of natural gas to higher order hydrocarbons.

The conversion of methane to higher order hydrocarbons at high temperatures, in excess of about 1200° C. is known. These processes are, however, energy intensive and have not been developed to the point where high yields are obtained even with the use of catalysts. Catalysts that are useful in these processes (e.g., chlorine) are corrosive under such operating conditions.

The catalytic oxidative coupling of methane at atmospheric pressure and temperatures of from about 500° to 1,000° C. has been investigated by G. E. Keller and M. M. Bhasin. These researchers reported the synthesis of ethylene via oxidative coupling of methane over a wide variety of metal oxides supported on an alpha alumina structure in *Journal of Catalysts* 73, 9–19 (1982). This article discloses the use of single component oxide catalysts that exhibited methane conversion to higher order hydrocarbons at rates no greater than four percent. The process by which Keller and Bhasin oxidized methane was cyclic, varying the feed composition between methane, nitrogen and air (oxygen) to obtain higher selectivities.

West German Patent No. DE 32370792 discloses the use of single supported component oxide catalysts. The process taught by this reference utilizes low oxygen partial pressure to give a high selectivity for the formation of ethane and ethylene. The conversion of methane to ethane and ethylene is, however, only on the order of from about four to about seven percent.

Methods for converting methane to higher order hydrocarbons at temperatures in the range of about 500° to about 1,000° C. are disclosed in U.S. Pat. Nos. 4,443,644; 4,443,645; 4,443,646; 4,443,647; 4,443,648; and 4,443,649. The processes taught by these references provide relatively high selectivities to higher order hydrocarbons but at relatively low conversion rates, on the order of less than about four percent overall conversion. In addition to synthesizing hydrocarbons, the processes disclosed in these references also produced a reduced metal oxide which must be frequently regenerated by contact with oxygen. The preferred processes taught by these references entail physically separate zones for a methane contacting step and for an oxygen contacting step, with the reaction promoter recirculating between the two zones.

U.S. Pat. Nos. 4,495,374 and 4,499,322 disclose processes for converting methane to higher order hydrocarbons using an oxidative synthesizing agent containing an alkali metal or compound thereof as a promoter. Both patents indicate that stability of the promoted synthesizing agent is enhanced by the presence of phosphorous.

Phosphate-containing catalysts have been disclosed for use in dehydrogenation process. For example, U.S. Pat. No. 4,255,283 discloses a process for the oxydehydrogenation of alkyl-substituted aromatic compounds to the corresponding alkenyl-substituted aromatics using a catalyst represented by the formula $$A_a M_b M^1_c M^{11}_d B_e P_y O_x$$

wherein A is an alkali metal and/or thallium; M is one or more of the elements of nickel, cobalt, copper, manganese, magnesium, zinc, calcium, niobium tantalum, strontium or barium; $M^1$ is one or more of the elements of iron, chromium, uranium, thorium, vanadium, titanium, lanthanum or the other rare earths; $M^{11}$ is one or more of the elements of tin, boron, lead, germanium, aluminum, tungsten or molybdenum; B is bismuth, tellurium, arsenic, antimony, cadmium, or combinations thereof; P is phosphorus; and wherein a through y have the following values: a=0 to 20; b=0 to 20; c=0 to 20; d=0 to 4; e=0.1 to 20; y=8 to 16; x=the number of oxygens required to satisfy the valence requirements of the other elements present; and wherein the sum of b+c+e is greater than 1. European application No. 0,000,617 discloses a process for producing indene using a catalyst represented by the formula $$M_a P_x O_y$$

wherein M is one or more elements selected from Mg, Sr, Ca, Ba, La, Ce, other rare earths, Cr, Mn, Fe, Co, Ni, Cu, Zn, Sn, Pb, Bi, Te, B, Al, Rh, Sb, As, U, Th, Ge and Ru; and wherein $0.1x \leq \Sigma a \leq 10x$, wherein $\Sigma a$ represents the sum of subscripts a of all of the metal ions and y is a number such that the valence requirements of the metal ions for oxygen is satisfied.

SUMMARY OF THE INVENTION

The present invention contemplates the provision of a process for converting methane to a higher order hydrocarbon comprising contacting a gaseous reactant comprising methane with a phosphate-containing catalyst for a sufficient period of time and an effective temperature to provide said higher order hydrocarbon, said catalyst being represented by the formula $$M_x PO_y$$

wherein

M is selected from the group consisting of Pb, Bi, Sb, Sn, Tl, In, Mn, Cd, Ge or a mixture of two or more thereof, x is from about 0.1 to about 10, and y is the number of oxygens needed to fulfill the valence requirements of the other elements.

DESCRIPTION OF THE PREFERRED EMBODIMENT

Catalyst

The phosphate-containing catalysts that are used in accordance with the inventive method are represented by the formula $$M_x PO_y$$

wherein M is selected from the group consisting of Pb, Bi, Sb, Sn, Tl, In, Mn, Cd, Ge or a mixture of two or more thereof; x is from about 0.1 to about 10, preferably from about 0.4 to about 4; and y is the number of oxygens needed to fulfill the valence requirements of the other elements. M is preferably Pb, Sb, Sn, Bi or a mixture of two or more thereof, more preferably Pb, Sb or a mixture of Pb and Sb.

In a particularly advantageous embodiment, the oxidation state of M is not at its highest level, nor is it at zero. M is therefore preferably selected from the group consisting of $Pb^{+2}$, $Bi^{+3}$, $Sb^{+3}$, $Sn^{+2}$, $Tl^{+1}$, $In^{+1}$, $In^{+3}$, $Mn^2$, $Mn^{+3}$, $Mn^{+4}$, $Mn^{+6}$, $Cd^{+2}$, $Ge^{+4}$, or mixtures of two or more thereof. More preferably, M is $Pb^{+2}$, $Bi^{+3}$, $Sb^{+3}$, $Sn^{+2}$ or a mixture of two or more thereof. Still more preferably, M is $Pb^{+2}$, $Sb^{+3}$ or a mixture thereof.

These catalysts may be used alone or supported on a carrier. Suitable carrier materials include silica, magnesium oxide, titanium dioxide, alumina, alumina-silica, silicon carbide, clay, zirconium oxide, and the like. In general, the support may be employed in amounts of up to about 95% by weight of the final catalyst composition. The catalyst may be incorporated in the carrier by coating, impregnation or coprecipitation using known techniques.

These catalysts may be prepared by coprecipitation or by other methods known in the art. Generally they are prepared by mixing an aqueous solution of compounds containing the metal components with an aqueous solution of phosphoric acid, forming a precipitate and drying this precipitate. Examples of the compounds containing the metal components that are useful include but are not limited to oxides, hydroxides, inorganic salts (.e.g, nitrates, phosphates, halides, carbonates, silicates, aluminates) and salts of organic acids (e.g., acetates, formates, butyrates, propionates, benzoates and the like).

The catalyst may be calcined to produce desirable physical properties such as attrition resistance, optimum surface area and particle size. It is generally preferred that the calcined catalyst be further heat-treated in the presence of oxygen at a temperature of above about 200° C. but below a temperature deleterious to the catalyst.

In order to further illustrate the preparation of the catalysts used in the inventive method, the following examples are provided. In the following examples as well as throughout the specification and claims, all parts and percentages are by weight and all temperatures are in degrees centrigrade unless otherwise indicated.

EXAMPLE 1

$Pb_3(PO_4)_2/SiO_2$ 29.81 gms. of $Pb(NO_3)_2$ were dissolved in water with stirring. 5.88 gms. of $H_3PO_4$ were added and a precipitate was formed. 135 gms. of $SiO_2$ were then added. The resulting slurry was heated at a temperature of 90° C. with stirring until a thickened paste-like mixture was formed. The mixture was then dried overnight at 120° C. The dried product was then calcined in air at 290° C. for 3 hours, then at 325° C. for 1.5 hours. This calcined product was then sifted. The 20-35 mesh particles were separated and calcined in air at 700° C. for 3 hours to provide the desired catalyst.

EXAMPLE 2

$Pb_3(PO_4)_2$ 29.8 gms. of $Pb(NO_3)_2$ were dissolved in 100 ml. of water with stirring. 5.88 gms. of $H_3PO_4$ were added to the solution with the result being the formation of a precipitate. The mixture was heated at a temperature of 90° C. with stirring until a thickened paste-like mixture was formed, then dried overnight at 120° C. The dried product was then calcined in air at 425° C. for 3 hours, then ground to a 20-35 mesh size to provide the desired catalyst.

EXAMPLE 3

$BiPO_4$ 24.25 gms. of $Bi(NO_3)_3$ were added to 100 ml. of water with stirring. 10 ml. of nitric acid were added to the mixture. 4.9 gms. of $H_3PO_4$ were added and a precipitate was formed. The mixture was heated at a temperature of 90° C. with stirring until a thickened paste-like material was formed, then dried overnight at 120° C. The dried product was then calcined in air at 425° C. for 3 hours, then ground to 20-35 mesh size to provide the desired catalyst. This catalyst had a surface area of 60 m²/gm.

EXAMPLE 4

$(Sb)_2PO_4/MgO$ 2.94 gms. of $H_3PO_4$, 12.09 gms. of MgO and 80.9 gms. of Nalco ISJ611 (a product of Nalco identified as a colloidal dispersion of $Sb_2O_5$ having a solids content of 12% by weight) were mixed to form a slurry. The slurry was dried at 120° C. to form a dried product. The dried product was calcined in air at a temperature of 290° C. for 3 hours, then at 425° C. for 3 hours to provide the desired catalyst.

EXAMPLE 5

$(Sb)_2PO_4/SiO_2$ 2.94 gms. of $H_3PO_4$, 45 gms. of $SiO_2$ and 80.9 gms of Nalco ISJ611 were mixed to form a slurry. The slurry was dried at 120° C. The dried product was calcined in air at 290° C. for 3 hours, then at 425° C. for 3 hours, to provide the desired catalyst.

EXAMPLE 6

$Sn_2P_2O_7/SiO_2$ 4 gms. of $Sn_2P_2O_7$ were slurried in 125 ml. of a 10% $H_3PO_4$ solution. 15 gms. of Nalco Silica Sol No. 2327 (a product of Nalco identified as an ammonium stabilized colloidal dispersion of $SiO_2$ having a solids content of 40% by weight) were added to the mixture. The mixture was heated at a temperature of 90° C. with stirring until a thickened paste-like mixture was formed, then dried at 120° C. The dried product was then ground to a 20-35 mesh size to provide the desired catalyst.

EXAMPLE 7

$SbPO_4/SiO_2$ 0.2 gms. of citric acid were added to 150 ml. of boiling water. 10 gms. of $Sb_2O_3$, 6.76 gms. of $H_3PO_4$ and 37.4 gms. of Nalco Silica Sol No. 2327 were added to the water. The mixture was heated with stirring until it was dry, it was then dried overnight at 120° C. The dried product was then calcined in air at 290° C. for 3 hours, then at 425° C. for 3 hours, then calcined at 610° C. for 3 hours to provide the desired catalyst. This catalyst had a surface area of 55.76 m²/gm.

EXAMPLE 8

$(Sb)_2PO_4$ 2.94 gms. of $H_3PO_4$ were slurried with 80.9 gms. of Nalco ISJ611. The slurry was dried at 120° C. to provide a dried product. The dried product was calcined in air at 290° C. for 3 hours, then at 425° C. for 3 hours to provide the desired catalyst.

EXAMPLE 9

$Pb_3(PO_4)_2/MgO$ 29.81 gms. of $Pb(NO_3)_2$ were dissolved in water with stirring. 5.88 gms. of $H_3PO_4$ were mixed with the solution, and a precipitate was formed. 36.27 gms. of MgO were added to the mixture. The mixture was heated and stirred until a thickened paste-like mixture was formed. This mixture was dried at 120° C. The dried mixture was calcined in air at 290° C. for 3 hours, then at 325° C. for 1.5 hours. The calcined mixture was then sifted. The 20-35 mesh particles were separated and calcined in air at 700° C. for 3 hours to provide the desired catalyst.

EXAMPLE 10

$Sb_2(PO_4)/SiO_2$ 62 gms. of Nalco Silica Sol No. 2326 (a product of Nalco identified as an ammonium stabilized silica sol having a solids content of 14.5% by weight), 40.5 gms. of Nalco ISJ611 and 1.47 gms. of $H_3PO_4$ were mixed with stirring, and dried overnight at 120° C. The dried product was calcined in air at 290° C. for 3 hours, then at 425° C. for 3 hours to provide the desired catalyst. This catalyst had a surface area of 146.13 m³/gm.

Process:

In the process of the present invention methane is contacted with a phosphate-containing catalyst, as described above, to form one or more higher order hydrocarbons. The higher order hydrocarbons may subsequently be further processed if necessary to yield substantially liquid hydrocarbon products.

Advantages over previously disclosed processes for the conversion of methane to higher order hydrocarbons include higher selectivities to higher molecular weight hydrocarbons, higher conversion rates, longer catalyst life and avoidance of corrosive and/or expensive gas phase promoters. Additionally, the process of the present invention is well-suited to a continuous process and also useful in the cyclic requirements of several known processes.

The present invention is particularly suitable for converting methane to ethane, ethylene or mixtures of ethane and ethylene. Natural gas which, as discussed above, generally contains a major amount of methane, can be treated in accordance with the inventive method. The other materials generally present in natural gas such as other hydrocarbons (e.g., ethane, propane, the butanes, and the pentanes), water, carbon dioxide, nitrogen, carbon monoxide and inert gases generally do not affect the efficiency of the inventive method.

The process of the present invention is an oxidative reaction. Gaseous oxygen may be provided as substantially pure oxygen or diluted with nitrogen, carbon dioxide, carbon monoxide, or other inert gases (e.g., argon, helium, etc.), or may be provided in air. Alternatively, the reaction may occur in the substantial absence of gaseous oxygen, oxygen for the reaction then being derived almost entirely from the oxygen in the phosphate-containing catalyst employed in the reaction.

The catalyst can be reoxidized by passing oxygen over it at an elevated temperature. Preferably a mixture of oxygen and an inert gas (e.g., air) is passed over the catalyst at the reaction temperature for a sufficient period of time (e.g., 15 minutes) to reoxidize the catalyst.

Preferably the gaseous reactant contains from about 15 volume percent to about 100 volume percent of methane and up to about 50 volume percent oxygen. A diluent gas may also be present in the gaseous reactant.

The process of the present invention is carried out by contacting the gaseous reactant with one of the catalysts described above in a fluid bed reactor, fixed bed reactor or any other suitable reactor configuration such as a moving bed reactor, swing reactor system or membrane reactor. The reaction can be conducted in a continuous or a batch-type mode. The reaction temperature is preferably in the range of from about 400° C. to about 1200° C., more preferably from about 700° C. to about 900° C.

The average contact time of the reactants with the catalyst is preferably from about 0.05 seconds to about 20 seconds, more preferably from about 0.1 seconds to about 2 seconds.

The reaction can be conducted at a pressure in the range of about 1 to about 100 atmospheres, preferably in the range of about 20 to about 60 atmospheres, more preferably at about 40 atmospheres.

Products of methane conversion in accordance with the present invention include ethane, ethylene and higher order hydrocarbons as well as byproduct water, carbon monoxide and carbon dioxide. The conversion rate of methane by the process of the present invention is as high as from about 15 percent to about 30 percent with reaction selectivity to the formation of higher order hydrocarbons in the range of from about 30 percent to about 70 percent. These conversion rates are significantly higher than those obtained by previously disclosed processes. Unconverted methane can be recycled to the reaction so as to increase the overall yield of higher order hydrocarbons by this process.

If the reaction contemplates recycling the unreacted natural gas, then the portion of the feed stream containing minor amounts of the ethane, propane, butane and pentane may change, depending on the efficiency of the product recovery apparatus. These alkanes need not be fully removed from the reactor feed stream.

The higher order hydrocarbons may be easily transported and have versatile applications in chemical processing as well as uses as fuels. In addition, these higher order hydrocarbons may be further processed to form substantially liquid hydrocarbons. The term "substantially liquid hydrocarbons" refers to hydrocarbons that are primarily in the liquid state at a temperature of 25° C. and a pressure of one atmosphere. For example in accordance with the processes disclosed in U.S. Pat. Nos. 4,100,218 and 4,120,910, these patents being incorporated herein by reference. In U.S. Pat. No. 4,100,218 ethane is subjected to thermal cracking at temperatures of from about 815° C. to about 875° C. to produce an olefin-rich effluent which is then cooled to a temperature between about 315° C. and about 650° C. and contacted with a zeolite so as to produce a liquid hydrocarbon product suitable for use as LPG, gasoline and/or aromatics concentrate. In U.S. Pat. No. 4,120,910 ethane is converted to liquid aromatic compounds with a process which comprises contacting, in the absence of added air or oxygen under conversion conditions, a gaseous paraffinic hydrocarbon feed containing ethane, with a catalyst comprising a crystalline aluminosilicate zeolite characterized by a constant index within the approximate range of 1 to 12 and a silica to alumina ratio of at least 12, said catalyst having incorporated therein from about 0.01 to 30 weight percent based on the total weight of the catalyst of a metal or metal oxide wherein said metal is selected from the group consisting of Group VIII, IIB and IB metals and mixtures thereof whereby ethane present in said gaseous feed is converted to aromatic compounds and recovering said aromatic compounds as liquids.

Other known processes are also available for the conversion of ethane and ethylene to ethanol, ethylene glycol, polyethylene, and other additional chemicals useful as fuels, fuel additives and lubricants. Thus, the process disclosed herein for upgrading low molecular weight alkanes to higher order hydrocarbons may be integrated with additional process steps for converting such alkanes to useful chemicals.

In order to further illustrate the inventive method, the results of the following test runs are provided. The reactions were run in a pulse mode with an on-line gas chromatograph used for analysis. Columns in the gas chromatograph are Poropak Q and molecular sieve to analyze for saturated and unsaturated hydrocarbons, carbon monoxide and carbon dioxide. Two cubic centimeters of a catalyst were placed in a quartz tube reactor having an 8 mm. diameter. The catalyst was held in place by quartz wool. Approximately 5 cc. of quartz chips were placed above and below the catalyst. The quartz tube was placed between the two halves of a suitcase type reactor and the temperature was set at the level indicated in Table I. The pressure was atmospheric. While "at rest" the catalyst was bathed in a stream of helium gas.

For test runs 1–3, a pulse of gaseous reactant (99% methane, 0.21% ethane, 0.07% propane, balance nitrogen) was inserted into the helium stream, advanced through the quartz reactor containing the catalyst at a flow rate of 2.6 sec/cc, and instantaneous product samples were analyzed with the gas chromatograph.

The conditions for test runs 4 and 5 were the same as for runs 1–3 except the gas hourly space velocity was 706 hrs.$^{-1}$.

Test runs 6 and 7 were run in a continuous mode using a gaseous mixture of methane, oxygen and nitrogen. This gaseous mixture was passed over the catalyst for 0.5 hour before testing. The gas hourly space velocity was 706 hrs.$^{-1}$. The gaseous mixture used in run 6 has the following volumetric ratios of $CH_4:O_2:N_2$ equal to 1:0.1:0.72. The volumetric ratios of $CH_4:O_2:N_2$ for run 7 were 1:0.21:2.59.

The results are indicated in Table I.

TABLE 1

| Run Number | Catalyst | Reaction Temperature (°C.) | Reactant Conversion (Percent) | Selectivity to $C_2 + C_3$ Hydrocarbons (Percent) |
|---|---|---|---|---|
| 1 | Product of Ex. 4 | 850 | 18 | 32 |
| 2 | Product of Ex. 5 | 750 | 19 | 40 |
| 3 | Product of Ex. 5 | 800 | 21 | 42 |
| 4 | Product of Ex. 7 | 750 | 19 | 40 |
| 5 | Product of Ex. 7 | 800 | 21 | 42 |
| 6 | Product of Ex. 7 | 829 | 17.3 | 29 |
| 7 | Product of Ex. 7 | 835 | 17.5 | 33 |

While the invention has been explained in relation to its preferred embodiments, it is to be understood that various modifications thereof will become apparent to those skilled in the art upon reading this specification. Therefore, it is to be understood that the invention disclosed herein is intended to cover such modifications as fall within the scope of the appended claims.

We claim:

1. A process for covering methane to a higher order hydrocarbon comprising contacting a gaseous reactant comprising methane with a phosphate-containing catalyst for a sufficient period of time and at an effective temperature to provide said phosphate-containing catalyst consisting essentially of the higher order hydrocarbon, said catalyst being represented by the formula $$M_xPO_y$$

wherein
M is selected from the group consisting of Pb, Bi, Sb, Sn, Tl, In, Mn, Cd, Ge or a mixture of two or more thereof,
x is from about 0.1 to about 10, and
y is the number of oxygens needed to fulfill the valence requirements of the other elements.

2. The process of claim 1 wherein M is Pb, Sb, Sn, Bi or a mixture of two or more thereof.

3. The process of claim 1 wherein M is Pb, Sb or a mixture of Ph and Sb.

4. The process of claim 1 wherein M is selected from the group consisting of $Pb^{+2}$, $Bi^{+3}$, $Sb^{+3}$, $Sn^{+2}$, $Tl^{+1}$, $In^{+1}$, $In^{+3}$, $Mn^{+2}$, $Mn^{+3}$, $Mn^{+4}$, $Mn^{+6}$, $Cd^{+2}$, $Ge^{+4}$, or mixtures of two or more thereof.

5. The process of claim 1 wherein x is from about 0.4 to about 4.

6. The process of claim 1 wherein said temperature is in the range of about 400° C. to about 1200° C.

7. The process of claim 1 wherein said temperature is in the range of about 700° C. to about 900° C.

8. The process of claim 1 wherein said period of time is from about 0.05 to about 20 seconds.

9. The process of claim 1 wherein said period of time is from about 0.1 to about 2 seconds.

10. The process of claim 1 wherein said gaseous reactant is at a pressure in the range of about 1 to about 100 atmospheres.

11. The process of claim 1 wherein said gaseous reactant further comprises oxygen.

12. The process of claim 1 wherein said gaseous reactant further comprises an inert gas.

13. The process of claim 1 wherein said gaseous reactant further comprises carbon dioxide.

14. The process of claim 1 wherein said gaseous reactant further comprises carbon monoxide.

15. The process of claim 1 wherein said gaseous reactant further comprises nitrogen, argon or helium.

16. The process of claim 1 wherein said gaseous reactant comprises natural gas.

17. The process of claim 1 wherein said higher order hydrocarbon comprises ethane, ethylene or a mixture of ethane and ethylene.

18. The process of claim 1 wherein said methane comprises from about 15% to 100% by volume of said gaseous reactant.

19. The process of claim 1 wherein said gaseous reactant contains up to about 50% by volume of oxygen.

20. The process of claim 1 wherein said catalyst is supported on an inert carrier.

21. The process of claim 20 wherein said inert carrier is magnesium oxide, titanium dioxide, alumina, silica, alumina-silica, silicon carbide, clay or zirconium oxide.

22. A process for converting methane to a higher order hydrocarbon comprising contacting a gaseous reactant comprising methane with a phosphate-containing catalyst at a temperature in the range of about 400° C. to about 1200° C. for a sufficient period of time to provide said higher order hydrocarbon, said phosphate-containing catalyst consisting essentially of the catalyst being represented by the formula $$M_xPO_y$$

wherein
M is selected from the group consisting of Pb, Bi, Sb, Sn or a mixture of two or more thereof,
x is from about 0.1 to about 10, and
y is the number of oxygens needed to fulfill the valence requirements of the other elements.

23. The process of claim 22 wherein said higher order hydrocarbons comprise ethane, ethylene or a mixture of ethane and ethylene.

24. The process of claim 22 wherein M is selected from the group consisting of $Pb^{+2}$, $Bi^{+3}$, $Sb^{+3}$, $Sn^{+2}$ or mixtures of two or more thereof.

25. The process of claim 22 wherein said period of time is from about 0.05 to about 20 seconds.

26. The process of claim 22 wherein said gaseous reactant is at a pressure in the range of about 1 to about 100 atmospheres.

27. A process for converting methane to a higher order hydocarbon comprising contacting a gaseous reactant comprising methane with a phosphate-containing catalyst for a sufficient period of time and at an effective temperature to provide said higher order hydrocarbon, said catalyst being represented by the formula $$M_xPO_y$$

wherein
M is selected from the group consisting of Tl, Cd, or a mixture thereof,
x is from about 0.1 to about 10, and
y is the number of oxygens needed to fulfill the valence requirements of the other elements.

* * * * *